US012079719B1

(12) United States Patent
Wei et al.

(10) Patent No.: US 12,079,719 B1
(45) Date of Patent: Sep. 3, 2024

(54) LIFELONG MACHINE LEARNING (LML) MODEL FOR PATIENT SUBPOPULATION IDENTIFICATION USING REAL-WORLD HEALTHCARE DATA

(71) Applicant: IQVIA Inc., Danbury, CT (US)

(72) Inventors: Guanhao Wei, Wayne, PA (US); Yunlong Wang, Malvern, PA (US); Li Zhou, Yardley, PA (US); Lynn Lu, San Diego, CA (US); Emily Zhao, Wayne, PA (US); Lishan Feng, Philadelphia, PA (US); Fan Zhang, King of Prussia, PA (US); Frank Jing, Beijing (CN); Yilian Yuan, North Wales, PA (US)

(73) Assignee: IQVIA Inc., Durham, NC (US)

( * ) Notice: Subject to any disclaimer, the term of this patent is extended or adjusted under 35 U.S.C. 154(b) by 1044 days.

(21) Appl. No.: 17/003,127

(22) Filed: Aug. 26, 2020

(51) Int. Cl.
*G06N 3/08* (2023.01)
*G06N 3/044* (2023.01)
(Continued)

(52) U.S. Cl.
CPC ............... *G06N 3/08* (2013.01); *G06N 3/044* (2023.01); *G06N 3/045* (2023.01); *G06N 3/047* (2023.01);
(Continued)

(58) Field of Classification Search
CPC .......... G06N 3/08; G06N 20/20; G06N 3/047; G06N 3/048; G06N 3/045; G06N 3/044;
(Continued)

(56) References Cited

U.S. PATENT DOCUMENTS 10,127,496 B1 * 11/2018 Fu ........................... G06N 3/045
11,023,730 B1 * 6/2021 Zhou ........................ G06N 3/08
(Continued)

FOREIGN PATENT DOCUMENTS

WO    WO-2020115730 A1 * 6/2020 ............. G06N 20/00
WO    WO-2020239234 A1 * 12/2020 ............. G06F 21/53

OTHER PUBLICATIONS

Sarajcev et al., "Wide & Deep Machine Learning Model for Transformer Health Analysis," in 4th Int'l Conf. Smart and Sustainable Techs. 1-6 (2019). (Year: 2019).*
(Continued)

*Primary Examiner* — Ryan C Vaughn
(74) *Attorney, Agent, or Firm* — John Maldjian, Esq.; David L. D'Amato, Esq.; Stevens & Lee PC

(57) ABSTRACT

A deep learning model implements continuous, lifelong machine learning (LML) based on a Bayesian neural network using an inventive framework including wide, deep, and prior components that employ diverse algorithms to leverage available real-world healthcare data differently to improve prediction performance. The outputs from each component of the framework are fed into a wide and shallow neural network and the posterior structure of the final model output may be utilized as a prior structure when the deep learning model is refreshed with new data in a deep learning process. Lifelong learning is implemented by dynamically integrating present learning from the wide and deep learning components with past learning from traditional tree models in the prior component into future predictions. Thus, the present Bayesian deep neural network-based LML model increases accuracy in identifying patient profiles by continuously learning, as new data become available, without forgetting prior knowledge.

19 Claims, 9 Drawing Sheets

(51) Int. Cl.
*G06N 3/045* (2023.01)
*G06N 3/047* (2023.01)
*G06N 3/048* (2023.01)
*G06N 5/01* (2023.01)
*G06N 20/20* (2019.01)
*G16H 10/60* (2018.01)
*G16H 40/20* (2018.01)
*G16H 50/70* (2018.01)
*G16H 70/20* (2018.01)
*G16H 70/40* (2018.01)
*G16H 70/60* (2018.01)

(52) U.S. Cl.
CPC .............. *G06N 3/048* (2023.01); *G06N 5/01* (2023.01); *G06N 20/20* (2019.01); *G16H 10/60* (2018.01); *G16H 40/20* (2018.01); *G16H 50/70* (2018.01); *G16H 70/20* (2018.01); *G16H 70/40* (2018.01); *G16H 70/60* (2018.01)

(58) Field of Classification Search
CPC .......... G06N 5/01; G16H 40/20; G16H 70/60; G16H 10/60; G16H 50/70; G16H 70/40; G16H 70/20
See application file for complete search history.

(56) References Cited

U.S. PATENT DOCUMENTS

| | | | |
|---|---|---|---|
| 11,295,197 B2* | 4/2022 | Murali | G06Q 30/0202 |
| 2017/0199972 A1* | 7/2017 | Hussam | G16H 10/60 |
| 2020/0085382 A1* | 3/2020 | Taerum | G06T 7/0016 |
| 2020/0152330 A1* | 5/2020 | Anushiravani | A61B 5/11 |
| 2020/0278650 A1* | 9/2020 | Bernstein | G06T 7/00 |
| 2020/0398079 A1* | 12/2020 | Adelsheim | G16H 50/20 |
| 2021/0073661 A1* | 3/2021 | Matlick | H04L 61/3025 |

OTHER PUBLICATIONS

Neal R.M. (1995) "Priors for Infinite Networks," In: Bayesian Learning for Neural Networks, vol. 118. Springer, New York, NY.

J. H. Lee, Y. Bahri, R. Novak, S. S. Schoenholz, J. Pennington, and J. Sohl-Dickstein, "Deep neural networks as gaussian processes", ICLR, 2018 (17 pages total).

"Universal approximation theorem" Retrieved from: https://en.wikipedia.org/wiki/Universal_approximation_theorem Retrieved on: Aug. 26, 2020 (4 pages total).

* cited by examiner

200

900

LIFELONG MACHINE LEARNING (LML) MODEL FOR PATIENT SUBPOPULATION IDENTIFICATION USING REAL-WORLD HEALTHCARE DATA

BACKGROUND

Many benefits from predictive analysis rely on the accuracy of the underlying analytical model. Such models are typically built based on objectives that are well defined as binary or multi-variate cohorts, for example: to identify patients with a certain rare disease or not; to identify patients who will have disease progression or not. Methods of model evaluation may be mathematically standard and therefore straightforward to understand. A hold-off sample is calculated based on the predicted positive patients and the number which is correctly predicted from actually observed positive patients. Popular models in predictive machine learning include tree models such as random forest (RF) and extreme gradient boost (XGB). Conventional enhancements to tree models may include stacking different tree models to achieve a more stable model. However, the accuracy of such enhanced models is reaching a maximum as all possible combinations of suitable hyper-parameters (e.g., number of layers, learning rate, etc.) are becoming exhausted.

SUMMARY

A deep learning model implements continuous, lifelong machine learning (LML) based on a Bayesian neural network using an inventive framework including wide, deep, and prior components that employ diverse algorithms to leverage available real-world healthcare data differently to improve prediction performance. The outputs from each component of the framework are fed into a wide and shallow neural network and the posterior structure of the final model output may be utilized as a prior structure when the deep learning model is refreshed with new data in a deep learning process. Lifelong learning is implemented by dynamically integrating present learning from the wide and deep learning components with past learning from traditional tree models in the prior component into future predictions. Thus, the present Bayesian deep neural network-based LML model increases accuracy in identifying patient profiles by continuously learning, as new data become available, without forgetting prior knowledge.

In an illustrative embodiment, the wide component uses demographic and clinical characteristics, aggregated diagnoses, and treatments as input features along with dense embeddings that are converted from sparse features such as doctor visits and drug usage. The features are concatenated as an input layer to a multi-level neural network that uses rectified linear unit (ReLU) activation functions. An output unit provides sigmoid output from the wide component.

The deep component employs sequential features such as diagnoses, procedure, and drug therapy as inputs to a plurality of LSTM (long short-term memory) models which are an exemplary type of recurrent neural network (RNN) architecture. The historical impact of features on patient medical history (e.g., diagnoses, procedures, drug therapies, etc.) may be utilized by the deep component to advantageously leverage sequential data. Sigmoid output from the deep component is provided by an output unit that is coupled to another multi-level neural network that uses ReLU activation functions.

The prior component can employ a fine-tuned deep learning model that is trained based on historical data in a previous period and a variably-implemented basket of traditional ML models including one or more of XGB (extreme gradient boosting), RF (random forest), LR (linear regression), and the like. Output from the traditional models is integrated with that from the wide and deep components in a shallow and wide neural network which provides a final sigmoid output from the Bayesian deep neural network-based LML model. The neural network in the deep component may be trained as a universal approximator for a large class of piecewise smooth functions and the wide component may enhance its capability to quickly capture the posterior structure of the model.

Advantageously, the present Bayesian deep neural network-based LML model can be expected to identify patient profiles more quickly and accurately from available real-world healthcare datasets. By implementing lifelong learning, fewer resources need to be expended for model training, testing, and validation and overall model performance is increased. In addition, because the inventive Bayesian deep neural network-based LML model remembers prior knowledge, instead of considering all histological information at one time, resources can be expended more specifically on the most recently updated data for training and/or validation to further improve overall model performance. Accordingly, computing resources utilized in implementations of machine learning such as processor cycles, memory, power, data transmission bandwidth and storage can be employed with greater efficiency as compared to conventional artificial intelligence/machine learning systems.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Furthermore, the claimed subject matter is not limited to implementations that solve any or all disadvantages noted in any part of this disclosure. It will be appreciated that the above-described subject matter may be implemented as a computer-controlled apparatus, a computer process, a computing system, or as an article of manufacture such as one or more computer-readable storage media. These and various other features will be apparent from a reading of the following Detailed Description and a review of the associated drawings.

DESCRIPTION OF THE DRAWINGS

Like reference numerals indicate like elements in the drawings. Elements are not drawn to scale unless otherwise indicated.

DETAILED DESCRIPTION

In the healthcare data analysis industry, machine learning algorithms are widely adopted to identify patients with certain profiles through real-world health data. Such predictive modeling approaches typically provide better results in proactively identifying patient candidates compared to rules-based methodologies which are often limited by how health data are recorded and captured for analysis.

Patient data are collected principally through insurance claims and detailed health profiles are not necessarily mandated for reporting on claim forms. Due to the potential for missed data points, analytical precision in directly reporting and identifying patients of interest can be limited. In addition, not all patient health claims are captured, or are only periodically captured during the course of a given treatment pathway. Using predictive modeling to classify patients with certain health profiles may therefore be the only effective solution in some scenarios.

Predictive modeling can be used to identify patients with rare diseases, particularly in situations where data for the patient population may not be effectively captured, or the disease may be susceptible to misdiagnosis such that some patient data get under-reported. Using predictive modeling can also provide an increase of "at-risk" patient candidates for treatment initiation or clinical trial screening. Such increased sample size can be expected to provide more stable analytical results.

Patient profiles obtained through predictive modeling can be used to evaluate treatment outcomes or effectiveness by better disease condition controls. The heightened ability to accurately find patients who might have a particular disease progression may help to promote proactive and effective treatment targeting.

Traditional machine learning methods typically utilize maximum likelihood-based or ensemble tree-based models which prefer features to be identified by domain expertise to reduce data complexity and strengthen data structures. Some of these traditional learning methods may have reached an accuracy ceiling that is not subject to further improvement. The present Bayesian deep neural network-based lifelong machine learning (LML) model is based on a Bayesian influencing concept that provides for updating model parameters dynamically through a sequence of model application and learning. The model implements lifelong learning by integrating wide and deep learning components with traditional tree models to leverage results from prior model learnings into future predictions. Such lifelong learning increases accuracy in identifying patient profiles as the model continues to learn from new data without forgetting prior knowledge.

Figure 1:
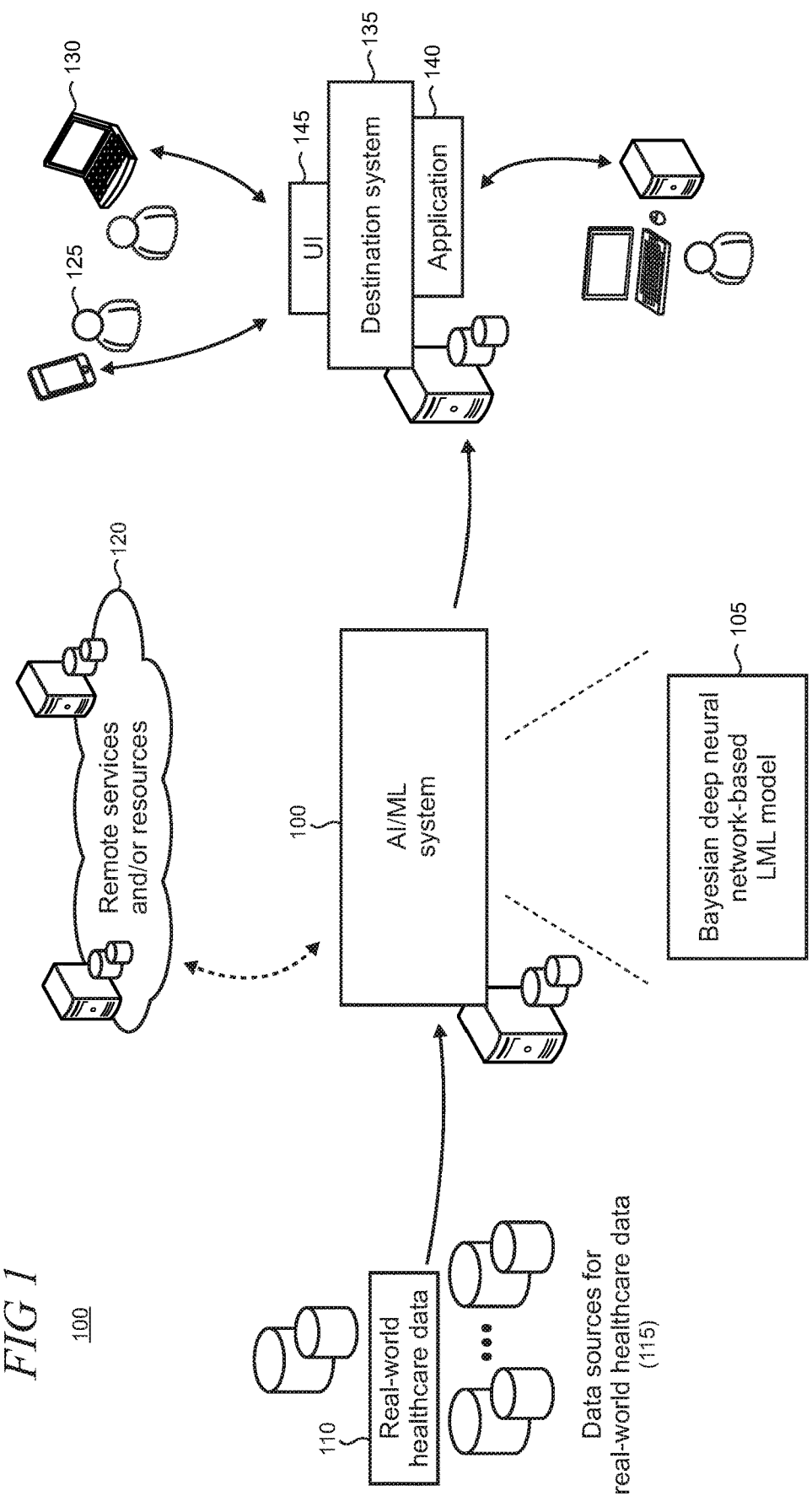
FIG. 1 shows an illustrative artificial intelligence/machine learning (AI/ML) system that utilizes a Bayesian deep neural network-based lifelong machine learning (LML) model.

Turning now to the drawings, FIG. 1 shows a high level overview of an illustrative artificial intelligence/machine learning (AI/ML) system 100 that utilizes a Bayesian deep neural network-based lifelong machine learning (LML) model 105 that may be implemented on computing infrastructure, as described below in the description below accompanying FIGS. 8 and 9. The AI/ML system is arranged to receive real-world healthcare data 110 for patients from one or more data sources 120. The data sources can be remotely located from the AI/ML system in some instances, and/or be operatively coupled to the AI/ML system over one or more communication networks (not shown) including, for example, local area network (LAN) and wide area network (WAN) infrastructure using wired or wireless connections.

The AI/ML system 100 may interact with remote services and/or resources (collectively identified by reference numeral 120) in some implementations in a distributed computing or cloud-based computing paradigms. In such cases, portions of storage, networking, or computational resources may be provided by, or using, the remote services/resources as suitable to implement various aspects of the AI/ML system functionality.

The AI/ML system 100 supports the Bayesian deep neural network-based LML model 105 that is configured to operate on real-world healthcare data 110 that are obtained from the data sources 115 and transformed into predictive solutions to identify patients that meet certain profiles, as discussed below in the text accompanying FIGS. 3 and 4. Users 125 of computing devices 130 such as personal computers, tablets, and smartphones, can interact with the predictive solutions on a destination system 135, for example, through an application 140 or user interface (UI) 145 that may support local and/or remote (i.e., cloud-based) usage scenarios.

Figure 2:
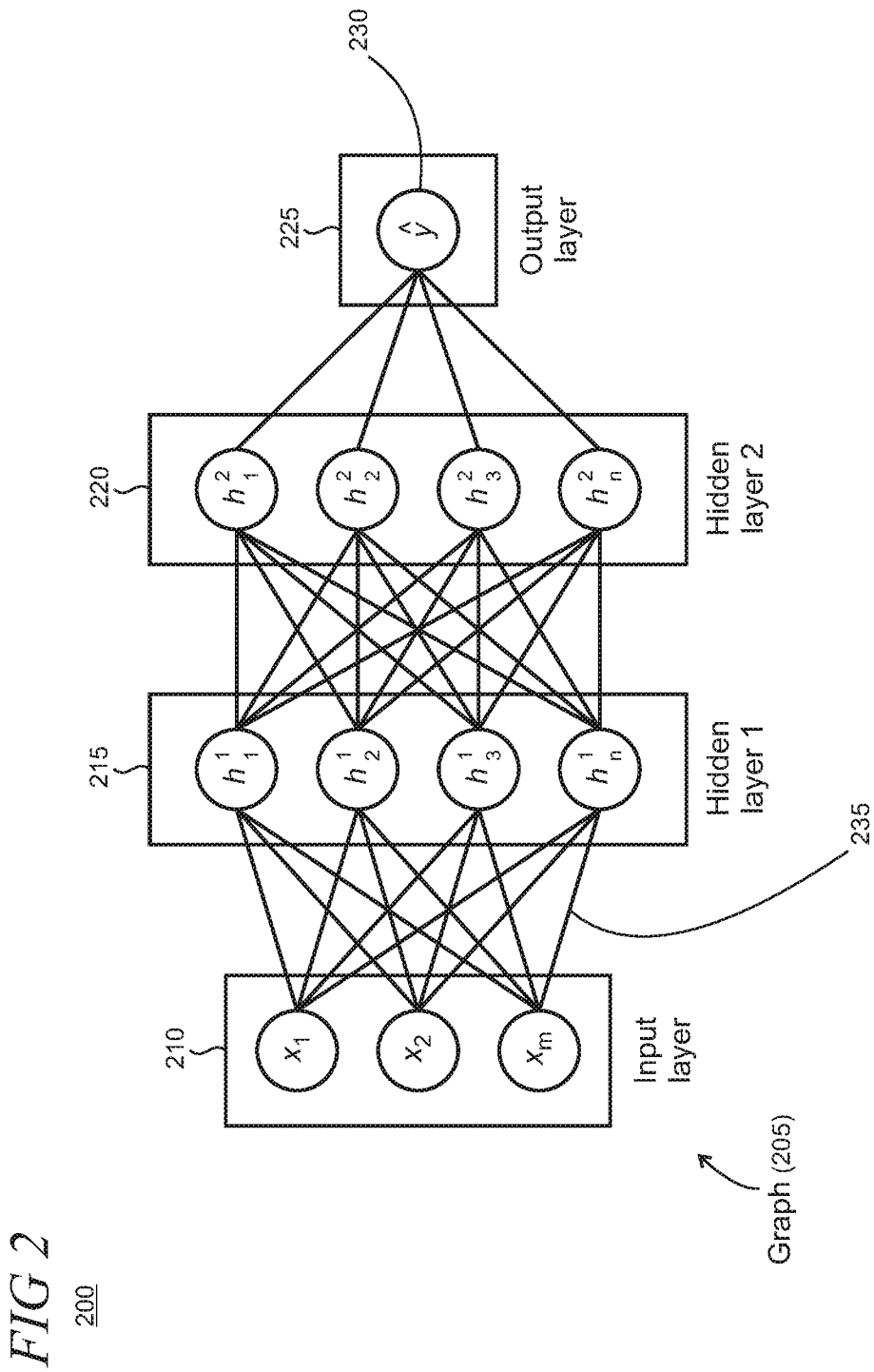
FIG. 2 shows an overview of an illustrative conventional Bayesian neural network providing a structured probabilistic model that is represented using a graph.

FIG. 2 shows an overview of an illustrative conventional Bayesian neural network 200 providing a structured probabilistic model that is represented using a graph 205. FIG. 2 is provided to establish terminology that is used in the detailed explanation of the inventive Bayesian deep neural network-based LML model 105 that follows in the description accompanying FIGS. 3-7 below. The Bayesian neural network 200 in this illustrative example has an input layer 210, two hidden layers 215 and 220, and an output layer 225. Each layer contains one or more nodes (alternatively referred to as "vertices") as representatively indicated by reference numeral 230. The vertices are connected by edges that represent weighting in the neural network, as representatively indicated by reference numeral 235. It is emphasized that the numbers of vertices, edges, and layers in the graph 205 are arbitrary in this particular example.

In graph 205, nodes 230 are either input values or functions for combining values. Edges 235 receive their weights as the data flow through the graph. Outbound edges from an input node are weighted with that input value; outbound nodes from a function node are weighted by combining the weights of the inbound edges using the specified function.

The function performed by each node in the neural net is called an activation function (also referred to as a transfer function). There are two steps in every activation function. First, all of the input values are combined in some way, typically as a weighted sum. Second, a nonlinear function is applied to that sum; this second function might change from layer to layer within a single neural network. As discussed below in the text accompanying FIGS. 3 and 4, the activation functions utilized in the Bayesian deep neural network-based LML model 105 include ReLU and sigmoid.

The hidden layers 215 and 220 add more nodes between the input layer 210 and output layer 225. Data in the input layer are labeled as x with subscripts $1, 2, 3, \ldots, m$. Nodes in the hidden layer are labeled as h with subscripts $1, 2, 3, \ldots, n$. The input data are shown as m $(x_1, x_2, \ldots, x_m)$, referred to as m features. A feature is a variable that has influence on a specific outcome. It is noted than m and n do not need to be equal.

Neural network 200 is considered Bayesian in this example because it implements Bayes' theorem that describes the probability of an event, based on prior knowledge of conditions that might be related to the event:

$$P(A|B) = \frac{P(B|A)P(A)}{P(B)} \quad (1)$$

P(A|B) is referred to as the posterior probability, or more generally simply "posterior" and P(A) is called the prior probability, or "prior." Thus, Bayes' theorem in eq. (1) may be stated in words as: Posterior=Likelihood*Prior/Evidence.

Figure 3:
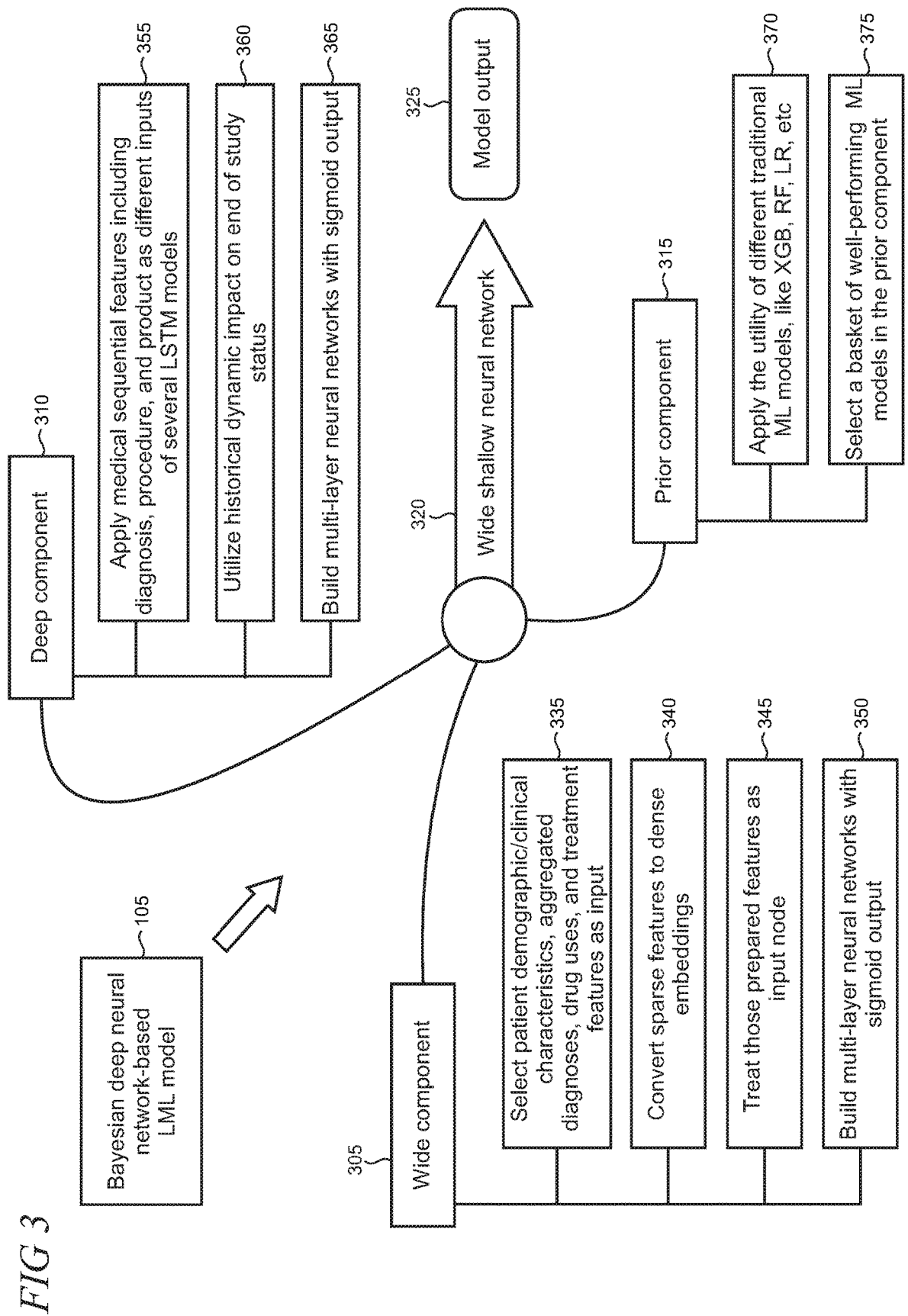
FIG. 3 shows illustrative functional blocks of the components that form an exemplary Bayesian deep neural network-based LML model.

FIG. 3 shows illustrative functional blocks of the components that make up the present Bayesian deep neural network-based LML model 105. The components include a wide component 305, a deep component 310, and a prior component 315. These components are each connected to a wide shallow neural network 320 which provide an output 325 from the model.

The functional elements comprising the wide component 305 include block 335 which is configured to utilize a number of features as input to the model 105. These features include patient demographics such as age and gender, clinical characteristics, aggregated diagnoses of patient conditions, drug and/or other therapeutics usage, and treatments.

Sparse medical data features, those in a dataset having many missing values (e.g., doctor visits and other episodic events which may have random time gaps between occurrences), are converted to dense embeddings at block 340. It may be appreciated that embedding provides a usable representation of sparse input features by translating a high-dimensional vector into a low-dimensional space. Embedding typically captures some of the semantics of the input by placing semantically similar inputs close together in the embedding space.

At block 345, the wide component 305 of the model 105 treats the prepared features as an input node to one or more multi-layer neural networks that are built at block 350. A sigmoid function provides a probability value between 0 and 1 as an output of the wide component.

In the deep component 310 of the Bayesian deep neural network-based LML model 105, medical sequential features that are represented by events that are typically captured as a temporal sequence (i.e., time-series) data in a patient record, such as diagnosis, procedure, and drug treatment, are applied as different input to several LSTM (long short-term memory) models in the deep component at block 355. At block 360 in the deep component, the LSTM models can utilize historical dynamic features collected from datasets representing sequential information to determine how those features impact patient medical history (e.g., diagnoses, procedures, drug therapies, etc.). As with the wide component 305, one or more multi-layer neural networks are built at block 365 and sigmoid function provides a probability value between 0 and 1 as an output of the deep component.

In the prior component 315 of the Bayesian deep neural network-based LML model 105, the utility of one or more different traditional ML models is applied at block 370. Such traditional models can include, for example, XGB (extreme gradient boosting), RF (random forest), LR (linear regression), and the like. At block 375, a basket of suitably well-performing models is selected for use in the prior component. The contents of the basket can be dynamically variable, and the constituent members can be tailored to meet the needs of a given implementation.

Figure 4:
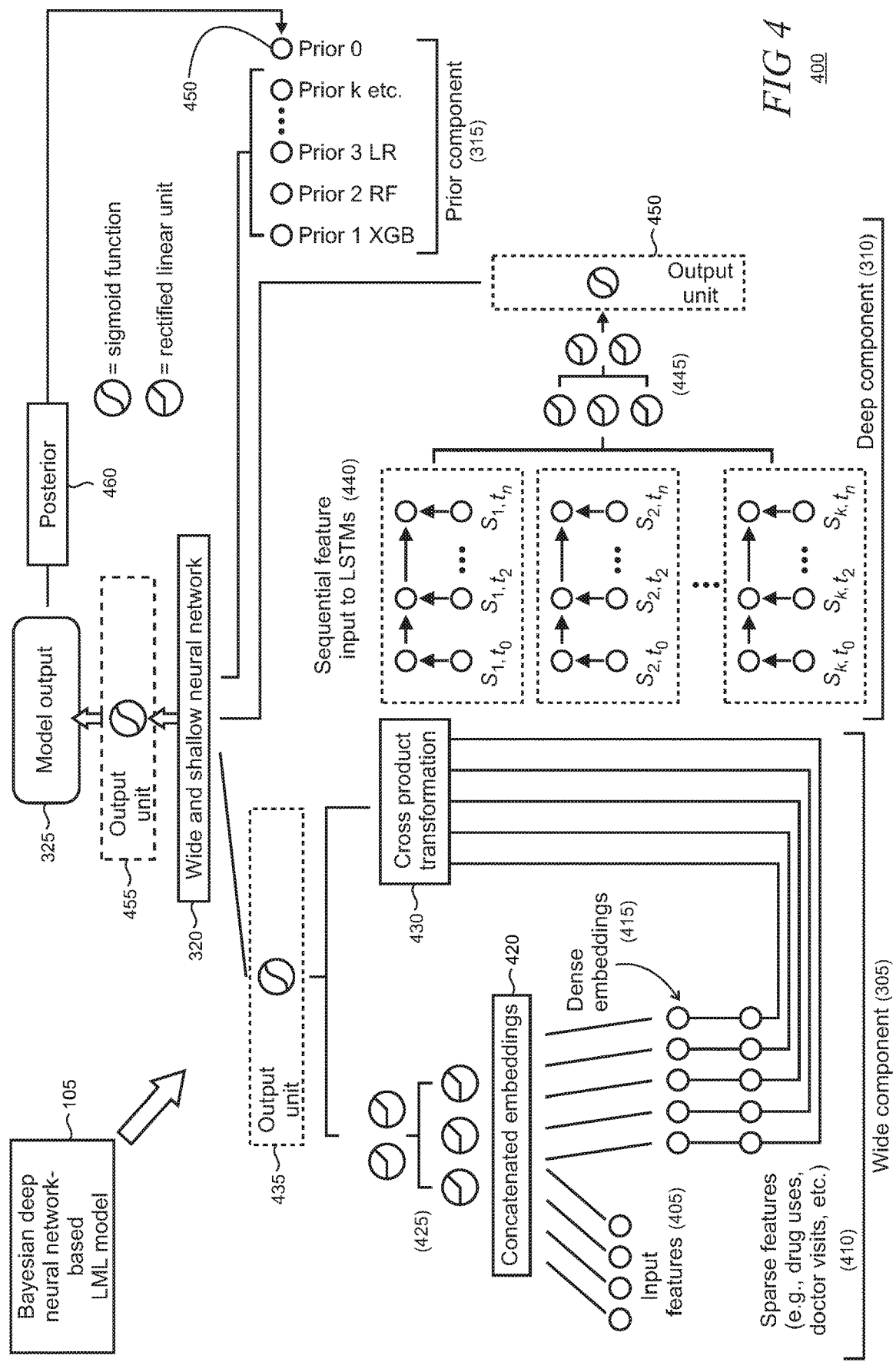
FIG. 4 shows an illustrative schematic of an exemplary Bayesian deep neural network-based LML model.

FIG. 4 shows an illustrative schematic 400 for the Bayesian deep neural network-based LML model 105. The schematic of the algorithm is deconstructed into the three different components with the wide component 305 located at the left, the deep component 310 in the middle, and the prior component 315 located at the right. At the onset, it is noted that feature cleaning and engineering are typically important steps that are performed prior to feature input to the model. This ensures that less correlated and a high percentage of missing and redundant features with substantially identical impacts are identified and filtered. Feature importance analysis can be applied to the different constituent ML models among the components to assist with top impact feature selection having less bias to improve model interpretation ability.

In the wide component 305, patient demographic clinical characteristics, aggregated diagnoses, drug uses, treatment features, and the like are selected as input features 405. Sparse features 410 are converted to dense embeddings 415. These prepared input features are concatenated in an embedding layer 420 which is utilized as an input to one or more multi-layer neural networks 425 that each utilize activation functions provided by a plurality of rectified linear units, as shown.

Cross product transformations of the input features is performed, as indicated by reference numeral 430. The output of neural network and cross product transformations are fed to an output unit 435 which provides an output to the wide and shallow neural network 320 using a sigmoid function.

In the deep component 310, medical sequential inputs such as diagnosis, procedure, and drug treatments can be applied as different inputs to several discrete LSTM models, is indicated by reference numeral 440. As noted above, the LSTM models are configured to utilize the historical dynamic of the sequential features on and of study status to thereby exploit temporal relationships. Subsequently, as with the wide component 305, one or more multi-level neural networks are built, and sigmoid output is generated at an output unit 450.

The prior component 315 is configured to use a plurality of traditional ML models in a basket of suitably well-performing models to provide prior structures to the Bayesian deep neural network-based LML model 105. Outputs from the wide, deep, and the plurality of prior components feed into the wide and shallow network 320 and the model output 325 is provided by the sigmoid function in the output unit 455. This enables the posterior structure 460 of the output to be well captured and be used as new priors in the next round of model refreshing as new features are observed.

The Bayesian deep neural network-based LML model 105 provides advantages over conventional deep neural networks by combining the wide, deep, and prior components in a single model. It is accepted in the AI/ML industry that deep neural networks may be theoretically capable of approximating any given function. Adding the wide component advantageously enhances the functionality of the deep component by enabling it to quickly capture the posterior structure. In addition, the wide component enables sequential or time-series data and/or longitudinal, or panel data structures (i.e., data arising from observations recorded for the same patients at multiple points in time) to be combined with prior structures to further advance the predictive power of the model.

Figure 5:
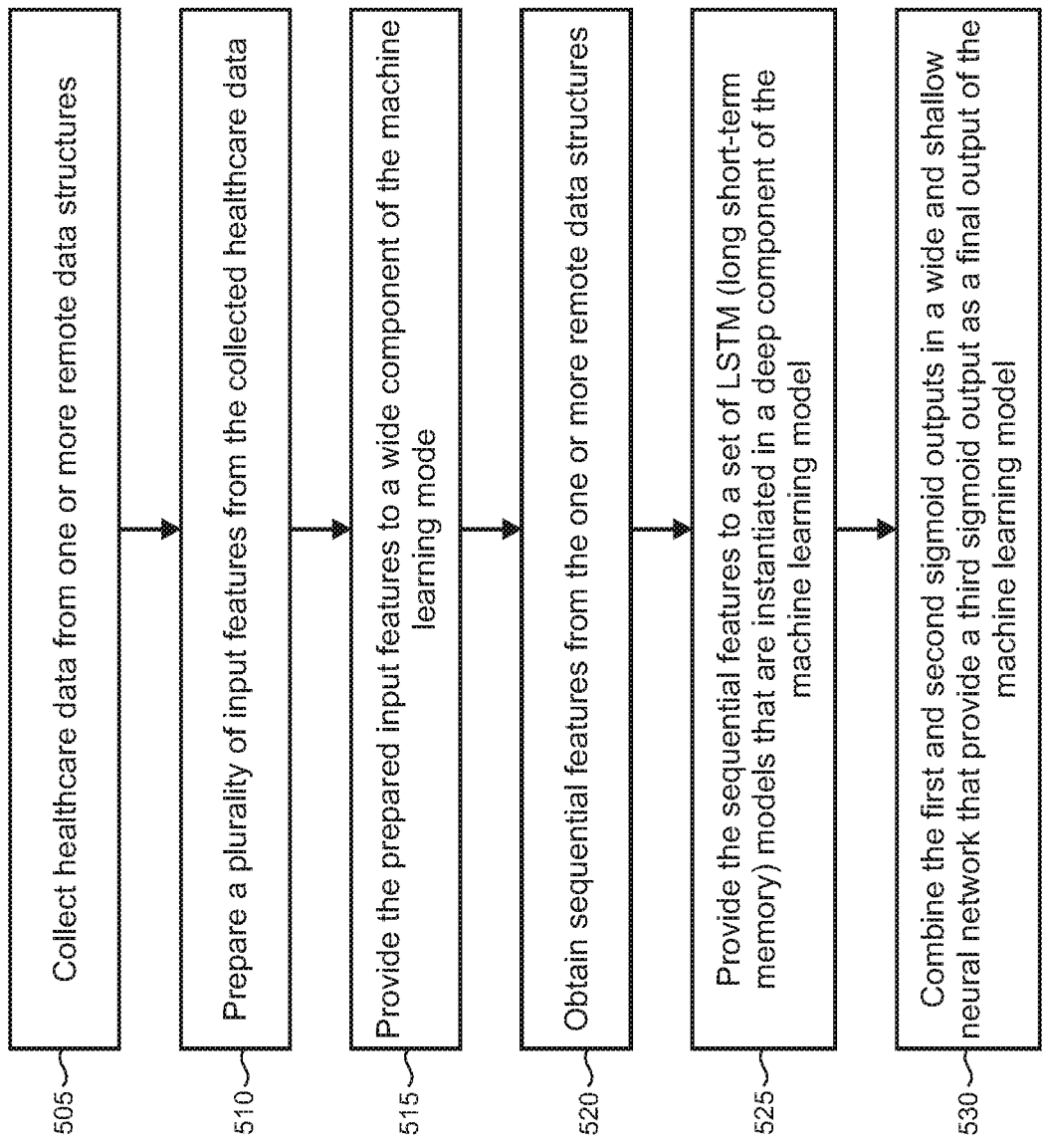
FIGS. 5-7 are flowcharts of illustrative methods performed by a computing device or server to implement a Bayesian deep neural network-based LML model.

FIG. 5 is a flowchart of an illustrative method 500 that may be performed by a computing device such as a personal computer, workstation, or server to implement the present Bayesian deep neural network-based LML model. Unless specifically stated, the methods or steps shown in the flowcharts and described in the accompanying text are not constrained to a particular order or sequence. In addition, some of the methods or steps thereof can occur or be performed concurrently and not all the methods or steps have to be performed in a given implementation depending on the requirements of such implementation and some methods or steps may be optionally utilized.

In step 505, healthcare data are collected from one or more remote data structures. In step 510, a plurality of input features is prepared from the collected healthcare data. In step 515, the prepared input features are provided to a wide component of the machine learning model. The wide component implements a first plurality of rectified linear unit (ReLU) activation functions arranged in a first multi-level neural network that provides a first sigmoid output based on the input features. In step 520, sequential features are obtained from the one or more remote data structures.

In step 525, the sequential features are provided to a set of LSTM (long short-term memory) models that are instantiated in a deep component of the machine learning model. The deep component implements a second plurality of ReLU activation functions arranged in a second multi-level neural network that provides a second sigmoid output based on the sequential features. In step 530, the first and second sigmoid outputs are combined in a wide and shallow neural network that provide a third sigmoid output as a final output of the machine learning model.

Figure 6:
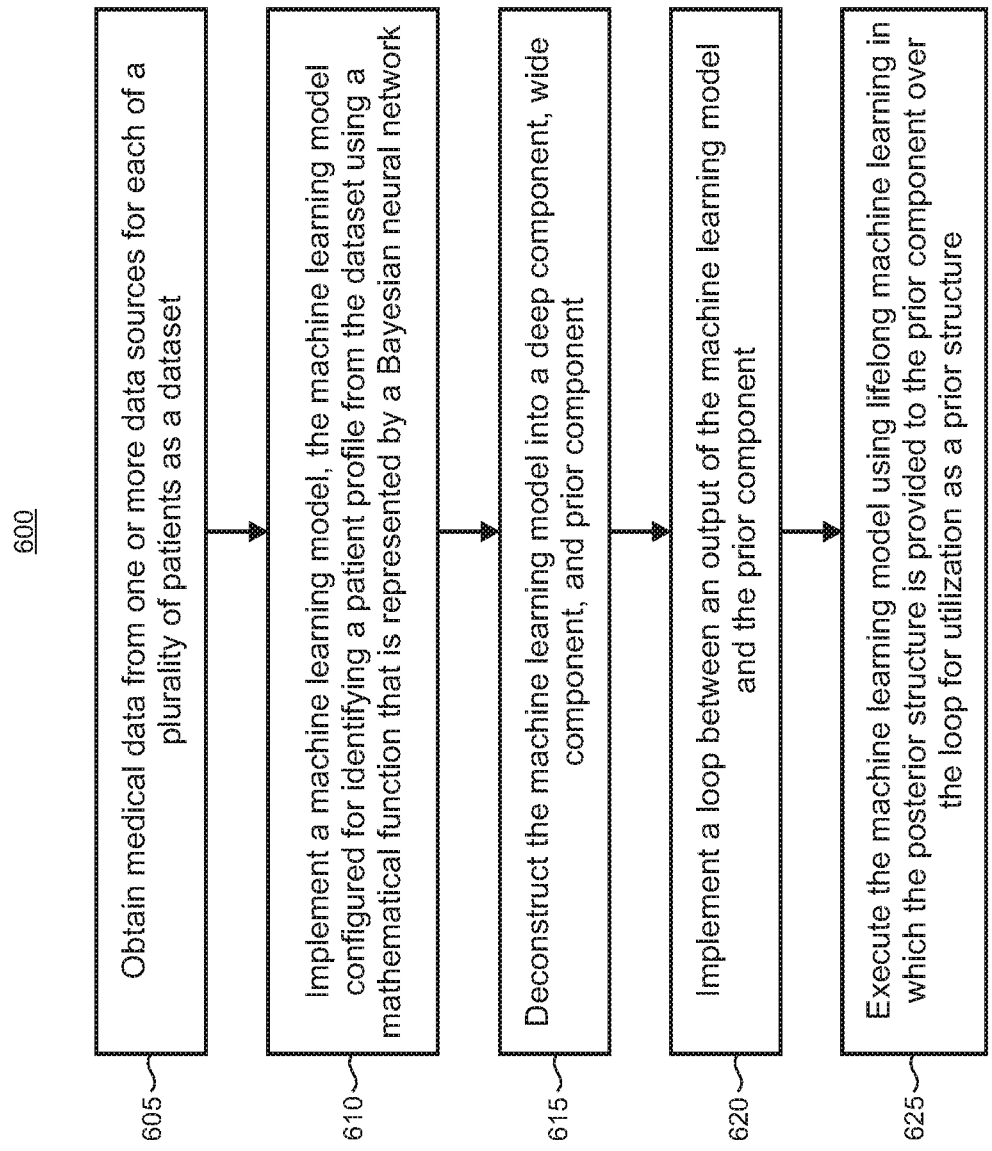

FIG. 6 is a flowchart of an illustrative method 600 that may be performed by a computing device such as a personal computer, workstation, or server to implement the present Bayesian deep neural network-based LML model. In step 605, medical data are obtained from one or more data sources for each of a plurality of patients as a dataset. In step 610, a machine learning model is implemented. The machine learning model configured for identifying a patient profile from the dataset using a mathematical function that is represented by a Bayesian neural network. In step 615, the machine learning model is deconstructed into a deep component, wide component, and prior component. The deep component provides a universal approximator feature to approximate the function that is represented by the Bayesian neural network. The wide component is configured to approximate a posterior structure of the machine learning model. The prior component is configured to provide prior structures to the machine learning model.

In step 620, a loop is implemented between an output of the machine learning model and the prior component. In step 625, the machine learning model is executed using lifelong machine learning in which the posterior structure is provided to the prior component over the loop for utilization as a prior structure.

Figure 7:
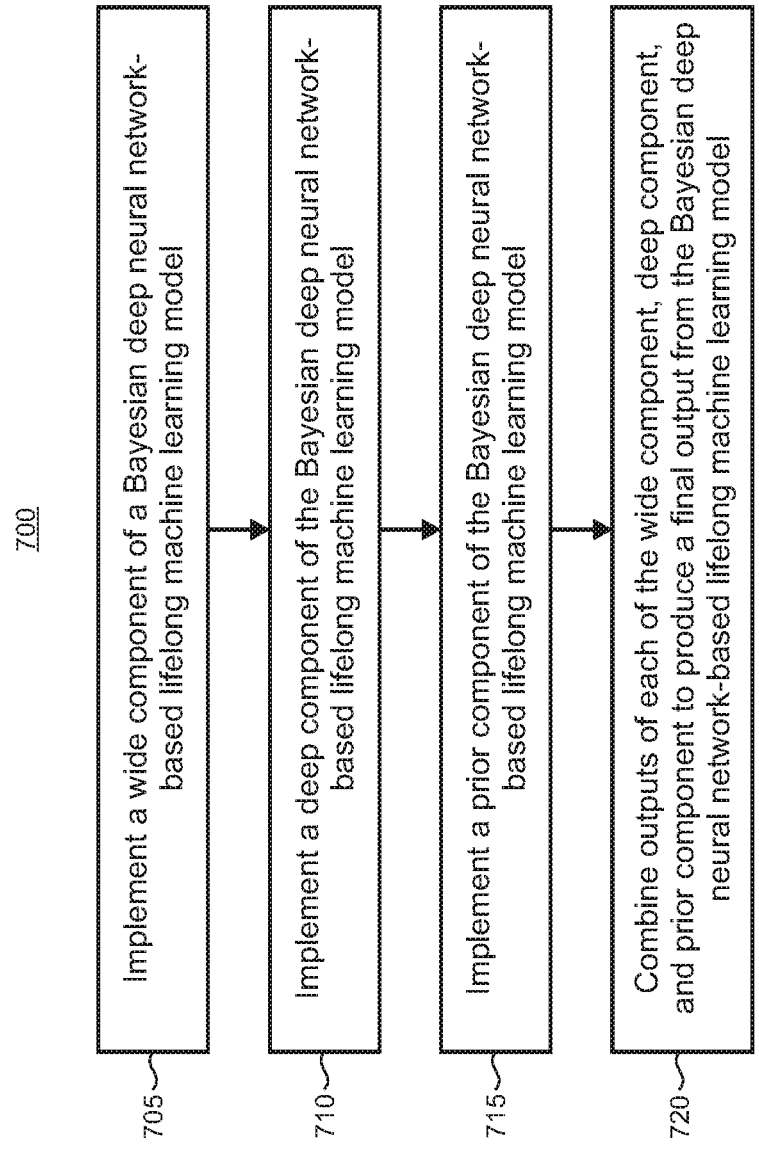

FIG. 7 is a flowchart of an illustrative method 700 that may be performed by a computing device such as a personal computer, workstation, or server to implement the present Bayesian deep neural network-based LML model. In step 705, a wide component of a Bayesian deep neural network-based lifelong machine learning model is implemented. The wide component is configured to utilize current non-sequential data from the healthcare dataset as non-sequential input features and provide predictions of identified patient profiles using a first multi-level neural network. In step 710, a deep component of the Bayesian deep neural network-based lifelong machine learning model is implemented. The deep component is configured to utilize current sequential data from the healthcare dataset as sequential input features and provide predictions of identified patient profiles using a second multi-level neural network.

In step 715, a prior component of the Bayesian deep neural network-based lifelong machine learning model is implemented. The prior component provides prior predictions of identified patient profiles from data in the healthcare dataset. In step 720, the outputs of each of the wide component, deep component, and prior component are combined to produce a final output from the Bayesian deep neural network-based lifelong machine learning model. The current final output is iteratively used as a prior prediction of identified patient profiles to implement lifelong machine learning.

Figure 8:
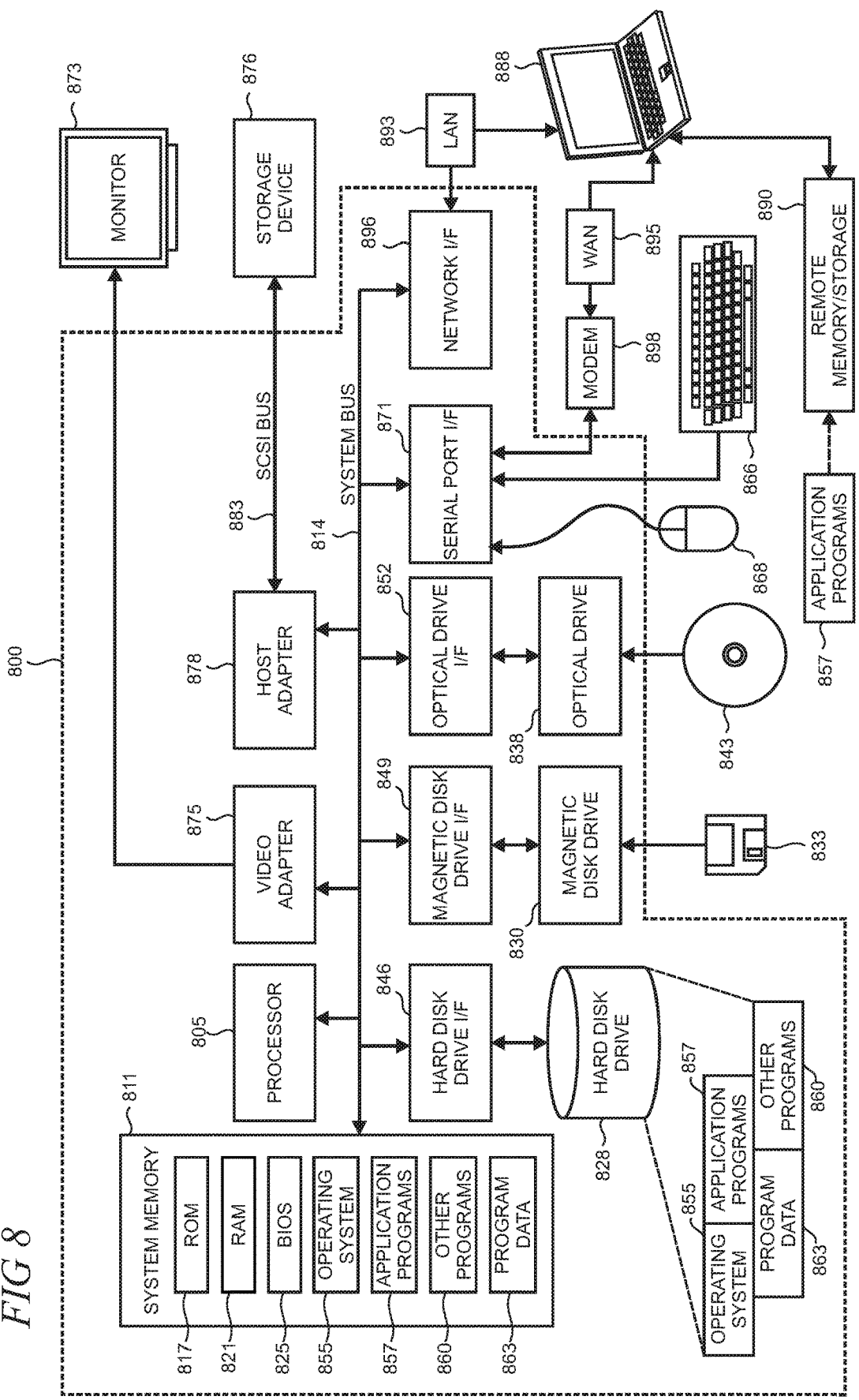
FIG. 8 is a block diagram of an illustrative architecture of a computing system such as a PC (personal computer) or server that may be used at least in part to implement a Bayesian deep neural network-based LML model.

FIG. 8 is a simplified block diagram of an illustrative architecture of a computer system 800 such as a PC or server with which the present Bayesian deep neural network-based LML model may be implemented. Computer system 800 includes a processor 805, a system memory 811, and a system bus 814 that couples various system components including the system memory 811 to the processor 805. The system bus 814 may be any of several types of bus structures including a memory bus or memory controller, a peripheral bus, or a local bus using any of a variety of bus architectures. The system memory 811 includes read only memory (ROM) 817 and random-access memory (RAM) 821. A basic input/output system (BIOS) 825, containing the basic routines that help to transfer information between elements within the computer system 800, such as during startup, is stored in ROM 817. The computer system 800 may further include a hard disk drive 828 for reading from and writing to an internally disposed hard disk (not shown), a magnetic disk drive 830 for reading from or writing to a removable magnetic disk 833 (e.g., a floppy disk), and an optical disk drive 838 for reading from or writing to a removable optical disk 843 such as a CD (compact disc), DVD (digital versatile disc), or other optical media. The hard disk drive 828, magnetic disk drive 830, and optical disk drive 838 are connected to the system bus 814 by a hard disk drive interface 846, a magnetic disk drive interface 849, and an optical drive interface 852, respectively. The drives and their associated computer-readable storage media provide non-volatile storage of computer-readable instructions, data structures, program modules, and other data for the computer system 800. Although this illustrative example includes a hard disk, a removable magnetic disk 833, and a removable optical disk 843, other types of computer-readable storage media which can store data that is accessible by a computer such as magnetic cassettes, Flash memory cards, digital video disks, data cartridges, random access memories (RAMs), read only memories (ROMs), and the like may also be used in some applications of the present Bayesian deep neural network-based LML model. In addition, as used herein, the term computer-readable storage media includes one or more instances of a media type (e.g., one or more magnetic disks, one or more CDs, etc.). For purposes of this specification and the claims, the phrase "computer-readable storage media" and variations thereof, are intended to cover non-transitory embodiments, and do not include waves, signals, and/or other transitory and/or intangible communication media.

A number of program modules may be stored on the hard disk, magnetic disk 833, optical disk 843, ROM 817, or RAM 821, including an operating system 855, one or more application programs 857, other program modules 860, and program data 863. A user may enter commands and information into the computer system 800 through input devices such as a keyboard 866 and pointing device 868 such as a mouse. Other input devices (not shown) may include a microphone, joystick, game pad, satellite dish, scanner, trackball, touchpad, touchscreen, touch-sensitive device, voice-command module or device, user motion or user gesture capture device, or the like. These and other input devices are often connected to the processor 805 through a serial port interface 871 that is coupled to the system bus 814, but may be connected by other interfaces, such as a parallel port, game port, or universal serial bus (USB). A monitor 873 or other type of display device is also connected to the system bus 814 via an interface, such as a video adapter 875. In addition to the monitor 873, personal computers typically include other peripheral output devices (not shown), such as speakers and printers. The illustrative example shown in FIG. 8 also includes a host adapter 878, a Small Computer System Interface (SCSI) bus 883, and an external storage device 876 connected to the SCSI bus 883.

The computer system 800 is operable in a networked environment using logical connections to one or more remote computers, such as a remote computer 888. The remote computer 888 may be selected as another personal computer, a server, a router, a network PC, a peer device, or other common network node, and typically includes many or all of the elements described above relative to the computer system 800, although only a single representative remote memory/storage device 890 is shown in FIG. 8. The logical connections depicted in FIG. 8 include a local area network (LAN) 893 and a wide area network (WAN) 895. Such networking environments are often deployed, for example, in offices, enterprise-wide computer networks, intranets, and the Internet.

When used in a LAN networking environment, the computer system 800 is connected to the local area network 893 through a network interface or adapter 896. When used in a WAN networking environment, the computer system 800 typically includes a broadband modem 898, network gateway, or other means for establishing communications over the wide area network 895, such as the Internet. The broadband modem 898, which may be internal or external, is connected to the system bus 814 via a serial port interface 871. In a networked environment, program modules related to the computer system 800, or portions thereof, may be stored in the remote memory storage device 890. It is noted that the network connections shown in FIG. 8 are illustrative and other means of establishing a communications link between the computers may be used depending on the specific requirements of an application of the present Bayesian deep neural network-based LML model.

Figure 9:
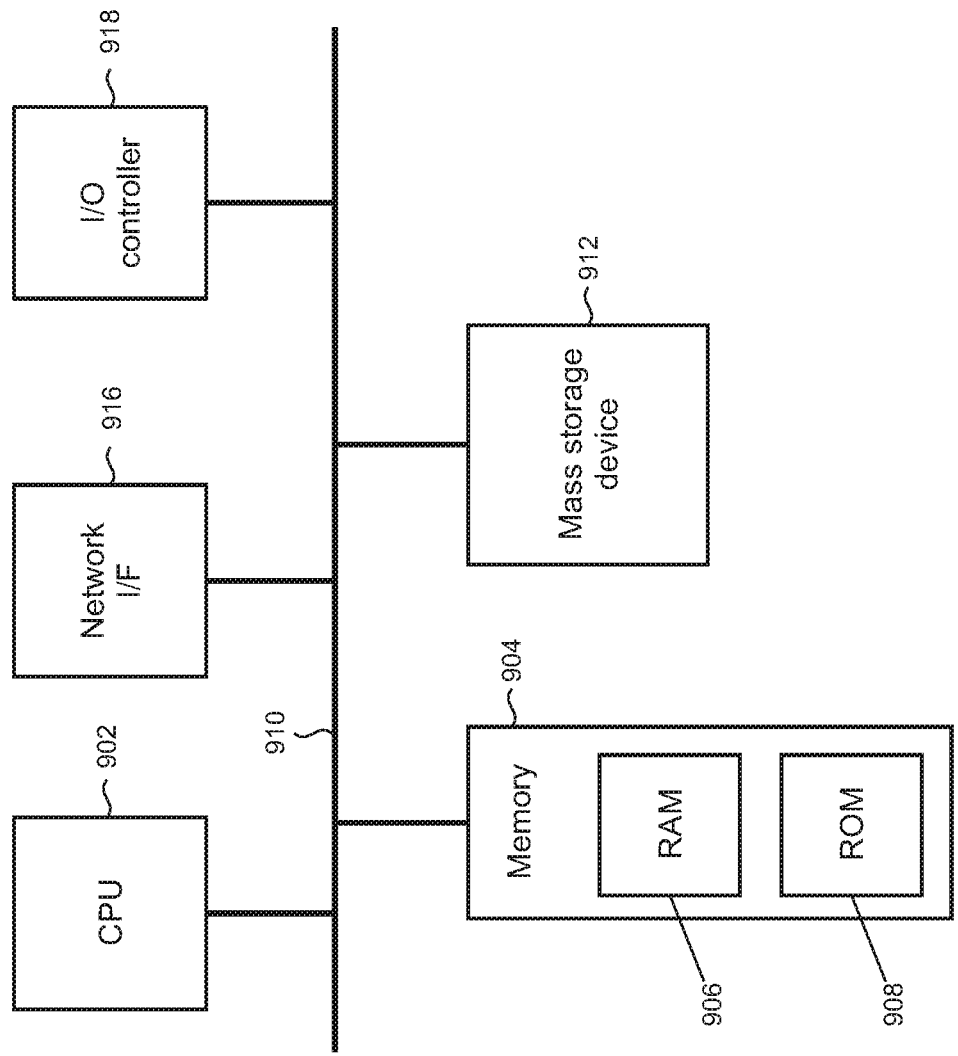
FIG. 9 is a simplified block diagram of an illustrative architecture of a computing device that may be used at least in part to implement a Bayesian deep neural network-based LML model.

FIG. 9 shows an illustrative architecture 900 for a client computing device such as a laptop computer or personal computer for the present Bayesian deep neural network-based LML model. The architecture 900 illustrated in FIG. 9 includes one or more processors 902 (e.g., central processing unit, dedicated Artificial Intelligence chip, graphics processing unit, etc.), a system memory 904, including RAM (random access memory) 906 and ROM (read only memory) 908, and a system bus 910 that operatively and functionally couples the components in the architecture 900. A basic input/output system containing the basic routines that help to transfer information between elements within the architecture 900, such as during startup, is typically stored in the ROM 908. The architecture 900 further includes a mass storage device 912 for storing software code or other computer-executed code that is utilized to implement applications, the file system, and the operating system. The mass storage device 912 is connected to the processor 902 through a mass storage controller (not shown) connected to the bus 910. The mass storage device 912 and its associated computer-readable storage media provide non-volatile storage for the architecture 900. Although the description of computer-readable storage media contained herein refers to a mass storage device, such as a hard disk or CD-ROM drive, it may be appreciated by those skilled in the art that computer-readable storage media can be any available storage media that can be accessed by the architecture 900.

By way of example, and not limitation, computer-readable storage media may include volatile and non-volatile, removable and non-removable media implemented in any method or technology for storage of information such as computer-readable instructions, data structures, program modules, or other data. For example, computer-readable media include, but are not limited to, RAM, ROM, EPROM (erasable programmable read only memory), EEPROM (electrically erasable programmable read only memory), Flash memory or other solid state memory technology, CD-ROM, DVD, HD-DVD (High Definition DVD), Blu-ray Disk or other optical storage, magnetic cassette, magnetic tape, magnetic disk storage or other magnetic storage device, or any other medium which can be used to store the desired information and which can be accessed by the architecture 900.

According to various embodiments, the architecture 900 may operate in a networked environment using logical connections to remote computers through a network. The architecture 900 may connect to the network through a network interface unit 916 connected to the bus 910. It may be appreciated that the network interface unit 916 also may be utilized to connect to other types of networks and remote computer systems. The architecture 900 also may include an input/output controller 918 for receiving and processing input from a number of other devices, including a keyboard, mouse, touchpad, touchscreen, control devices such as buttons and switches or electronic stylus (not shown in FIG. 9). Similarly, the input/output controller 918 may provide output to a display screen, user interface, a printer, or other type of output device (also not shown in FIG. 9).

It may be appreciated that the software components described herein may, when loaded into the processor 902 and executed, transform the processor 902 and the overall architecture 900 from a general-purpose computing system into a special-purpose computing system customized to facilitate the functionality presented herein. The processor 902 may be constructed from any number of transistors or other discrete circuit elements, which may individually or collectively assume any number of states. More specifically, the processor 902 may operate as a finite-state machine, in response to executable instructions contained within the software modules disclosed herein. These computer-executable instructions may transform the processor 902 by specifying how the processor 902 transitions between states, thereby transforming the transistors or other discrete hardware elements constituting the processor 902.

Encoding the software modules presented herein also may transform the physical structure of the computer-readable storage media presented herein. The specific transformation of physical structure may depend on various factors in different implementations of this description. Examples of such factors may include, but are not limited to, the technology used to implement the computer-readable storage media, whether the computer-readable storage media are characterized as primary or secondary storage, and the like. For example, if the computer-readable storage media are implemented as semiconductor-based memory, the software disclosed herein may be encoded on the computer-readable storage media by transforming the physical state of the semiconductor memory. For example, the software may transform the state of transistors, capacitors, or other discrete circuit elements constituting the semiconductor memory. The software also may transform the physical state of such components in order to store data thereupon.

As another example, the computer-readable storage media disclosed herein may be implemented using magnetic or optical technology. In such implementations, the software presented herein may transform the physical state of magnetic or optical media, when the software is encoded therein. These transformations may include altering the magnetic characteristics of particular locations within given magnetic media. These transformations also may include altering the physical features or characteristics of particular locations within given optical media to change the optical characteristics of those locations. Other transformations of physical media are possible without departing from the scope and spirit of the present description, with the foregoing examples provided only to facilitate this discussion.

In light of the above, it may be appreciated that many types of physical transformations take place in the architecture 900 in order to store and execute the software components presented herein. It also may be appreciated that the architecture 900 may include other types of computing devices, including wearable devices, handheld computers, embedded computer systems, smartphones, PDAs, and other types of computing devices known to those skilled in the art. It is also contemplated that the architecture 900 may not include all of the components shown in FIG. 9, may include other components that are not explicitly shown in FIG. 9, or may utilize an architecture completely different from that shown in FIG. 9.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A computing device configured for implementing a machine learning model using a Bayesian neural network, comprising:
    one or more processors; and
    one or more hardware-based non-transitory computer-readable memory devices storing instructions which, when executed by the one or more processors, cause the computing device to:
        collect current healthcare data from one or more remote data structures;
        prepare a plurality of non-sequential input features from the collected current healthcare data;
        provide the prepared non-sequential input features to a wide component of the machine learning model, wherein the wide component implements a first plurality of rectified linear unit (ReLU) activation functions arranged in a first multi-level neural network;
        obtain sequential features from the current healthcare data;
        provide the sequential features to a set of LSTM (long short-term memory) models that are instantiated in a deep component of the machine learning model, in which the deep component implements a second plurality of ReLU activation functions arranged in a second multi-level neural network;
        combine the wide component, the deep component, and a prior component of the machine learning model in a wide and shallow neural network that provides a posterior structure of the machine learning model, the prior component comprising one or more machine learning and/or deep learning models trained on historical healthcare data; and
        provide the posterior structure to the one or more models of the prior component for use in connection with subsequent healthcare data.

2. The computing device of claim 1 in which the prior component comprises a basket of machine learning models.

3. The computing device of claim 2 in which the basket of machine learning models includes one or more tree models.

4. The computing device of claim 3 in which the one or more tree models comprise one of XGB (extreme gradient boosting), RF (random forest), or LR (linear regression).

5. The computing device of claim 1 in which the final output comprises identification of one or more patient profiles.

6. The computing device of claim 5 in which the executed instructions further cause the computing device to provide the final output to a remote destination system that includes a user interface configured to enable users to interact with the one or more identified patient profiles.

7. One or more hardware-based non-transitory computer-readable memory devices storing instructions which, when executed by one or more processors disposed in a computing device, cause the computing device to:
    obtain current medical data from one or more data sources for each of a plurality of patients as a dataset;
    implement a machine learning model, the machine learning model configured for identifying a patient profile from the dataset using a mathematical function that is represented by a Bayesian neural network;
    deconstruct the machine learning model into a deep component, wide component, and prior component, wherein the deep component provides a universal approximator feature to approximate the function that is represented by the Bayesian neural network and receives sequential input features of the current medical data, wherein the wide component is configured to receive non-sequential input features of the current medical data, and wherein the prior component comprises one or more machine learning and/or deep learning models trained on historical medical data, and wherein the wide component, the deep component and the prior component are combined in a wide and shallow neural network;
    implement a loop between an output of the machine learning model and the prior component, wherein the output is a posterior structure of the machine learning model; and
    execute the machine learning model using lifelong machine learning in which the posterior structure is provided to the one or more models of the prior component over the loop for utilization in connection with subsequent medical data.

8. The one or more hardware-based non-transitory computer-readable memory devices of claim 7 in which the wide component and the deep component each includes a discrete neural network.

9. The one or more hardware-based non-transitory computer-readable memory devices of claim 8 in which the deep component comprises a plurality of discrete recurrent neural network (RNN) architectures.

10. The one or more hardware-based non-transitory computer-readable memory devices of claim 9 in which the discrete RNN architectures comprise respective LSTM (long short-term memory) models that are configured to receive sequential features.

11. The one or more hardware-based non-transitory computer-readable memory devices of claim 10 in which outputs from the LSTM models feed the neural network in the deep component.

12. The one or more hardware-based non-transitory computer-readable memory devices of claim 7 in which sparse features are converted to dense embeddings as inputs to the wide component.

13. The one or more hardware-based non-transitory computer-readable memory devices of claim 7 in which sparse features are transformed using a cross product and the transformed features are provided in parallel with output from the neural network in the wide component to an output unit that includes a sigmoid function.

14. A method implemented on a computing device for identifying patient profiles from a healthcare dataset that is dynamically updated with data, the method comprising:
   implementing a wide component of a Bayesian deep neural network-based lifelong machine learning model, the wide component configured to utilize current non-sequential data from the healthcare dataset as non-sequential input features and provide predictions of identified patient profiles using a first multi-level neural network;
   implementing a deep component of the Bayesian deep neural network-based lifelong machine learning model, the deep component configured to utilize current sequential data from the healthcare dataset as sequential input features and provide predictions of identified patient profiles using a second multi-level neural network;
   implementing a prior component of the Bayesian deep neural network-based lifelong machine learning model, the prior component comprising one or more machine learning and/or deep learning models trained on a historical healthcare dataset; and
   combining the wide component, deep component, and prior component in a wide and shallow neural network to produce a final output and a posterior structure from the Bayesian deep neural network-based lifelong machine learning model,
   wherein the posterior structure is iteratively used as a new prior prediction model of the prior component in connection with subsequent healthcare data, to implement lifelong machine learning.

15. The method of claim 14 in which the sequential data comprise diagnosis, procedure, and drug therapy.

16. The method of claim 14 in which the non-sequential data comprise one of demographic data, clinical characteristics, aggregated diagnoses, drug uses, and treatments.

17. The method of claim 14 in which the prior component uses one or more tree-based machine learning models.

18. The method of claim 14 further including applying feature importance analysis to one or more of the multi-level neural networks.

19. The method of claim 14 further including identifying and filtering redundant features from the healthcare dataset.

* * * * *